(12) United States Patent
Wu et al.

(10) Patent No.: US 10,696,614 B2
(45) Date of Patent: Jun. 30, 2020

(54) PHOTOCATALYTIC REDUCTION OF CARBON DIOXIDE TO METHANOL OR CARBON MONOXIDE USING CUPROUS OXIDE

(71) Applicant: UCHICAGO ARGONNE, LLC, Chicago, IL (US)

(72) Inventors: Yimin Wu, Schaumburg, IL (US); Tijana Rajh, Naperville, IL (US); Ian McNulty, Romeoville, IL (US); Yuzi Liu, Woodridge, IL (US)

(73) Assignee: UChicago Argonne, LLC, Chicago, IL (US)

( * ) Notice: Subject to any disclaimer, the term of this patent is extended or adjusted under 35 U.S.C. 154(b) by 50 days.

(21) Appl. No.: 15/858,307

(22) Filed: Dec. 29, 2017

(65) Prior Publication Data

US 2019/0202762 A1 Jul. 4, 2019

(51) Int. Cl.
| | | |
|---|---|---|
| *C07C 29/15* | (2006.01) | |
| *C01G 3/02* | (2006.01) | |
| *B01J 23/72* | (2006.01) | |
| *B01J 27/051* | (2006.01) | |
| *B01J 35/00* | (2006.01) | |
| *B01J 37/10* | (2006.01) | |
| *C01B 32/40* | (2017.01) | |
| *B01J 19/12* | (2006.01) | |

(Continued)

(52) U.S. Cl.
CPC ............ *C07C 29/15* (2013.01); *B01J 19/123* (2013.01); *B01J 19/127* (2013.01); *B01J 23/72* (2013.01); *B01J 27/051* (2013.01); *B01J 35/002* (2013.01); *B01J 35/004* (2013.01); *B01J 37/031* (2013.01); *B01J 37/04* (2013.01); *B01J 37/088* (2013.01); *B01J 37/10* (2013.01); *C01B 32/40* (2017.08); *C01G 3/02* (2013.01); *B01J 2219/0884* (2013.01); *B01J 2219/0892* (2013.01)

(58) Field of Classification Search
CPC ......... C07C 29/15; B01J 37/04; B01J 19/123; B01J 19/127; B01J 35/004; B01J 27/051; B01J 23/72; B01J 37/10; B01J 2219/0884; B01J 2219/0892; C01B 32/40; C01G 3/02
USPC .............................. 204/157.9, 157.47, 157.5
See application file for complete search history.

(56) References Cited

U.S. PATENT DOCUMENTS

| 8,313,634 B2 | 11/2012 | Bocarsly et al. |
| 8,500,987 B2 | 8/2013 | Teamey et al. |

(Continued)

FOREIGN PATENT DOCUMENTS

| CN | 107020103 A | * | 8/2017 | |
| WO | WO-2016058862 A1 | * | 4/2016 | ............ C07C 51/00 |

(Continued)

OTHER PUBLICATIONS

Zhao et al, "Cu2O Decorated with Cocatalyst MoS2 for Solar Hydrogen Production with Enhanced Efficiency under Visible Light," J. Phys. Chem. C, 2014, vol. 118, 14238-14245 (Year: 2014).*

(Continued)

*Primary Examiner* — Nicholas A Smith
*Assistant Examiner* — Colleen M Raphael
(74) *Attorney, Agent, or Firm* — Marshall, Gerstein & Borun, LLP

(57) ABSTRACT

Provided herein are methods of $CO_2$ reduction to methanol or CO using a $Cu_2O$ catalyst.

20 Claims, 2 Drawing Sheets

(51) Int. Cl.
B01J 37/04 (2006.01)
B01J 37/08 (2006.01)
B01J 37/03 (2006.01)

(56) References Cited

U.S. PATENT DOCUMENTS

| | | | |
|---|---|---|---|
| 8,568,581 B2 | 10/2013 | Sivasankar et al. | |
| 8,592,633 B2 | 11/2013 | Cole et al. | |
| 8,658,016 B2 | 2/2014 | Lakkaraju et al. | |
| 8,709,228 B2 | 4/2014 | Deguchi et al. | |
| 8,721,866 B2 | 5/2014 | Sivasankar et al. | |
| 8,845,878 B2 | 9/2014 | Cole et al. | |
| 8,961,774 B2 | 2/2015 | Cole et al. | |
| 9,090,976 B2 | 7/2015 | Bocarsly et al. | |
| 9,205,420 B2 | 12/2015 | Reece et al. | |
| 9,528,192 B1 | 12/2016 | Chen | |
| 9,545,625 B2 | 1/2017 | Andino et al. | |
| 2010/0213046 A1* | 8/2010 | Grimes | B01J 23/42 204/157.47 |
| 2013/0168228 A1* | 7/2013 | Ozin | B01J 35/004 204/157.9 |
| 2015/0167179 A1* | 6/2015 | Fleig | C25B 1/003 205/340 |
| 2016/0193595 A1* | 7/2016 | Nagpal | B01J 23/72 502/215 |
| 2016/0348256 A1* | 12/2016 | Dennis | C25B 3/04 |
| 2017/0225150 A1* | 8/2017 | Bakr | C25B 1/003 |
| 2018/0119296 A1* | 5/2018 | Geioushy | C25B 3/04 |
| 2018/0280942 A1* | 10/2018 | Chen | B01J 19/127 |
| 2019/0030523 A1* | 1/2019 | Chen | B01J 31/4023 |

FOREIGN PATENT DOCUMENTS

| | | | | | |
|---|---|---|---|---|---|
| WO | WO-2017108248 A1 | * | 6/2017 | .......... | B01J 19/0093 |
| WO | WO-2017108249 A1 | * | 6/2017 | .......... | B01J 19/0093 |

OTHER PUBLICATIONS

Quan et al, "High-Index Faceted Noble Metal Nanocrystals," Accounts of Chemical Research, vol. 46, No. 2, 2013, pp. 191-202 (Year: 2013).*

Stacchiola, "Tuning the Properties of Copper-Based Catalysts Based on Molecular in Situ Studies of Model Systems," Acc. Chem. Res. 2015, 48, 2151-2158 (Year: 2015).*

An et al., Cu2O/reduced graphene oxide composites for the photocatalytic conversion of CO2, ChemSusChem., 7:1086-93 (2014).

Angamuthu et al., Electrocatalytic CO2 conversion to oxalate by a copper complex, Science, 327(5963):313-5 (2010).

Aoun et al., A generalized method for high throughput in-situ experiment data analysis: An example of battery materials exploration, J. Power Sources, 279:246-51 (2015).

Asadi et al., Robust carbon dioxide reduction on molybdenum disulphide edges, Nat. Commun., 5:4470 (2014).

Bendavid et al., First-Principles Predictions of the Structure, Stability, and Photocatalytic Potential of Cu2O Surfaces, J. Phys. Chem. B, 117:15750-60 (2013).

Blöchl, Projector augmented-wave method, Phys. Rev. B, 50:17953-79 (1994).

Chen et al., Accelerating materials development for photoelectrochemical hydrogen production: Standards for methods, definitions, and reporting protocols, J. Mater. Res., 25:3-16 (2010).

Chen et al., Tin oxide dependence of the CO2 reduction efficiency on tin electrodes and enhanced activity for tin/tin oxide thin-film catalysts, J. Am. Chem. Soc., 134(4):1986-9 (2012).

Chueh et al., High-flux solar-driven thermochemical dissociation of CO2 and H2O using nonstoichiometric ceria, Science, 330(6012):1797-801 (2010).

Cui et al., A simple two-step electrodeposition of Cu2O/ZnO nanopillar solar cells, J. Phys. Chem. C, 114(14):6408-12 (2010).

Demas et al., Determination of the quantum yield of the ferrioxalate actinometer with electrically calibrated radiometers, J. Phys. Chem., 85:2766-71 (1981).

Gao et al., Partially oxidized atomic cobalt layers for carbon dioxide electroreduction to liquid fuel, Nature, 529(7584):68-71 (2016).

Graciani et al., Catalysis. Highly active copper-ceria and copper-ceria-titania catalysts for methanol synthesis from $CO_2$, Science, 345(6196):546-50 (2014).

Hammersley et al., Two-dimensional detector software: From real detector to idealised image or two-theta scan, High Press. Res., 14:235-48 (1996).

Handoko et al., Controllable proton and CO2 photoreduction over Cu2O with various morphologies, Int. J. Hydrogen Energy, 38(29):13017-22 (2013).

Jiang et al., Turning carbon dioxide into fuel, Philos. Trans A Math Phys. Eng. Sci., 368(1923):3343-64 (2010).

Kainz et al., Asymmetric copper-catalyzed C—N cross-couplings induced by visible light, Science, 351(6274):681-4 (2016).

Klahr et al., Competitive photoelectrochemical methanol and water oxidation with hematite electrodes, ACS Appl. Mater. Interfaces, 7:7653-60 (2015).

Kothandaraman et al., Conversion of CO2 from Air into Methanol Using a Polyamine and a Homogeneous Ruthenium Catalyst, J. Am. Chem. Soc., 138(3):778-81 (2016).

Kresse et al., Efficiency of ab-initio total energy calculations for metals and semiconductors using a plane-wave basis set, Comput. Mater. Sci., 6:15-50 (1996).

Kresse et al., From ultrasoft pseudopotentials to the projector augmented-wave method, Phys. Rev. B, 59:1758-75 (1999).

Kuhn et al., Chemical actinometry (IUPAC Technical Report), Pure Appl. Chem., 76:2105-46 (2004).

Kwon et al., Shape effects of cuprous oxide particles on stability in water and photocatalytic water splitting, J. Mater. Chem. A, 3:156-62 (2015).

Li et al., Electroreduction of carbon monoxide to liquid fuel on oxide-derived nanocrystalline copper, Nature, 508(7497):504-7 (2014).

Liao et al., Morphology-dependent interactions of ZnO with Cu nanoparticles at the materials' interface in selective hydrogenation of CO2 to CH3OH, Angew. Chem. Int. Ed. Engl., 50(9):2162-5 (2011).

Liu et al., Carbon Dioxide Conversion to Methanol over Size-Selected Cu4 Clusters at Low Pressures, J. Am. Chem. Soc., 137(27):8676-9 (2015).

Liu et al., Nanowire-bacteria hybrids for unassisted solar carbon dioxide fixation to value-added chemicals, 15(5):3634-9 (2015).

Liu et al., Water splitting. Metal-free efficient photocatalyst for stable visible water splitting via a two-electron pathway, Science, 347(6225):970-4 (2015).

Loiudice et al., Tailoring Copper Nanocrystals towards C2 Products in Electrochemical CO2 Reduction, Angew. Chem. Int. Ed. Engl., 55(19):5789-92 (2016).

Mistry et al., Highly selective plasma-activated copper catalysts for carbon dioxide reduction to ethylene, Nat. Commun., 7:12123 (2016).

Morales et al., Electrodeposition of Cu2O: an excellent method for obtaining films of controlled morphology and good performance in Li-ion batteries, Electrochem. Solid-State Lett., 8:A159-62 (2005).

Morris et al., Molecular approaches to the photocatalytic reduction of carbon dioxide for solar fuels, Acc. Chem. Res., 42(12):1983-94 (2009).

Paracchino et al., Highly active oxide photocathode for photoelectrochemical water reduction, Nat. Mater., 10(6):456-61 (2011).

Paracchino et al., Ultrathin films on copper(I) oxide water splitting photocathodes: a study on performance and stability, Energy Environ. Sci., 5:8673-81 (2012).

Paria et al., Copper in photocatalysis, ChemCatChem 6,:2477-83 (2014).

Perdew et al., Generalized Gradient Approximation Made Simple, Phys. Rev. Lett., 77:3865-8 (1996).

Qiu et al., Artificial Photosynthesis on TiO2-Passivated InP Nanopillars, Nano. Lett., 15(9):6177-81 (2015).

(56) References Cited

OTHER PUBLICATIONS

Rajh et al., Surface Modification of Small Particle TiO2 Colloids with Cysteine for Enhanced Photochemical Reduction: An EPR Study, J. Phys. Chem., 100:4538-45 (1996).

Reske et al., Particle size effects in the catalytic electroreduction of CO2 on Cu nanoparticles, J. Am. Chem. Soc., 136(19):6978-86 (2014).

Roberts et al., High selectivity for ethylene from carbon dioxide reduction over copper nanocube electrocatalysts, Angew. Chem. Int. Ed. Engl., 54(17):5179-82 (2015).

Sekizawa et al., Artificial Z-scheme constructed with a supramolecular metal complex and semiconductor for the photocatalytic reduction of CO2, J. Am. Chem. Soc., 135(12):4596-9 (2013).

Singh et al., Thermodynamic and achievable efficiencies for solar-driven electrochemical reduction of carbon dioxide to transportation fuels, Proc. Natl. Acad. USA, 112(45):E6111-8 (2015).

Song et al., High-Selectivity Electrochemical Conversion of CO2 to Ethanol using a Copper Nanoparticle/N-Doped Graphene Electrode, ChemistrySelect, 1:6055-61 (2016).

Styring, Artificial photosynthesis for solar fuels, Faraday Discuss., 155:357-76 (2012).

Tamaki et al., Photocatalytic CO2 reduction with high turnover frequency and selectivity of formic acid formation using Ru(II) multinuclear complexes, Proc. Natl. Acad. Sci. USA, 109(39):15673-8 (2012).

Tang et al., The importance of surface morphology in controlling the selectivity of polycrystalline copper for CO2 electroreduction, Phys. Chem. Chem. Phys., 14(1):76-81 (2012).

Tran et al., Recent advances in hybrid photocatalysts for solar fuel production, Energy Environ. Sci., 5:5902-18 (2012).

Wang et al., Controlled synthesis of concave Cu2O microcrystals enclosed by {hhl} high-index facets and enhanced catalytic activity, J. Mater. Chem. A, 1:282-7 (2013).

Wang, New developments in transmission electron microscopy for nanotechnology, Adv. Mater., 15:1497-514 (2003).

Watari et al., Differential stress induced by thiol adsorption on facetted nanocrystals, Nat. Mater., 10:862-6 (2011).

Winarski et al., A hard X-ray nanoprobe beamline for nanoscale microscopy, J. Synchrotron. Rad., 19:1056-60 (2012).

Yoshida et al., Visualizing gas molecules interacting with supported nanoparticulate catalysts at reaction conditions, Science, 335:317-9 (2012).

Yu et al., Carbon dioxide fixation into chemicals (methyl formate) at high yields by surface coupling over a Pd/Cu/ZnO nanocatalyst, J. Am. Chem. Soc., 129(20):6360-1 (2007).

Yu et al., Enhanced activity and stability of carbon-decorated cuprous oxide mesoporous nanorods for CO2 reduction in artificial photosynthesis, ACS Catal., 6:6444-54 (2016).

\* cited by examiner

PHOTOCATALYTIC REDUCTION OF CARBON DIOXIDE TO METHANOL OR CARBON MONOXIDE USING CUPROUS OXIDE

STATEMENT OF GOVERNMENT SUPPORT

The United States Government has rights in this invention pursuant to Contract No. DE-AC02-06CH11357 between the U.S. Department of Energy and UChicago Argonne, LLC representing Argonne National Laboratory.

BACKGROUND

Development of sustainable and clean sources of energy alongside the mitigation of greenhouse gas emissions rank among the greatest challenges facing our planet in this century. Eventual depletion of fossil fuels and the observed rapid increase in associated $CO_2$ emissions add additional urgency to these challenges. Mitigation of $CO_2$ emissions combined with the generation of sustainable fuels is highly desirable. Current methods for $CO_2$ reduction include electroreduction, hydrogenation at elevated temperature, and photocatalysis using $TiO_2$. Electroreduction is a process that requires a large overpotential and electrical energy input; in addition, the use of electricity as a secondary form of energy is inefficient due to losses associated with conversion of energy from primary sources as well as problematic storage of said energy. Hydrogenation of $CO_2$ involves the use of hydrogen which raises cost and safety issues. $TiO_2$ reductions of $CO_2$ have only been performed with limited success and the ability of $TiO_2$ to absorb light is limited exclusively to UV light, which composes only 5% of the solar spectrum. Thus, a need exists for other methods for reducing $CO_2$.

SUMMARY

Provided herein are methods of converting $CO_2$ to methanol comprising irradiating $CO_2$, water, and $Cu_2O$ having a (i i 0) facet to form methanol, wherein i is 1 to 12.

In various cases, the irradiating comprises exposure to ultraviolet to visible light. In some cases, the irradiating comprises exposure to light having one or more wavelengths from 200 to 650 nm.

In various embodiments, the water is present as a liquid. In some aspects, the water is present as water vapor.

In some cases, the (i i 0) facet is a (110) facet. In some embodiments, the $Cu_2O$ having a (110) facet is octahedral, truncated cubic, or a mixture thereof. In various embodiments, the irradiating comprises exposure to ultraviolet to visible light. In some embodiments, the irradiating comprises exposure to light having one or more wavelengths from 200 to 650 nm.

In some cases, the disclosed methods exhibit a quantum efficiency of at least 50%. In some embodiments, the quantum efficiency is at least 70%.

In various cases, $CO_2$ is continuously flowed through a suspension of the $Cu_2O$ in water during the irradiating.

In some embodiments, the $Cu_2O$ having a (i i 0) facet is prepared by a method comprising admixing copper acetate, sodium hydroxide, glucose, and a surfactant and heating the admixture to 60° C. for 30-90 minutes to form the $Cu_2O$ having a (i i 0) facet. In various cases, the surfactant comprises sodium dodecyl sulfate.

Also provided herein are methods of converting $CO_2$ to CO comprising irradiating $CO_2$, water, and $MoS_2$ adsorbed onto $Cu_2O$ to form CO, wherein the $Cu_2O$ has a (i i 0) facet, and i is 1 to 12. In various cases, the irradiating comprises exposure to ultraviolet to visible light. In some cases, the irradiating comprises exposure to light having one or more wavelengths from 200 to 650 nm. In various cases, the (i i 0) facet is a (110) facet. In some embodiments, the $Cu_2O$ having a (110) facet is octahedral, truncated cubic, or a mixture thereof.

DETAILED DESCRIPTION

Cu compounds are promising as photocatalysts with good multielectron transfer properties because of their loosely bonded d-electrons. While they have only just begun to be explored, Cu based catalysts show great potential for facilitating $CO_2$ activation and conversion to CO or ethylene by electroreduction, as well as water splitting, solar cells and Li ion batteries. Furthermore, $Cu_2O$ is an inexpensive material based on relatively abundant elements. $Cu_2O$ is a direct-gap semiconductor with a bandgap of 2.1 eV enabling the absorption of visible light that constitutes most of the solar spectrum. It shows intrinsic p-type conductivity due to the presence of negative-charged Cu vacancies and possesses one of the lowest electron affinities of the elements, enabling $Cu_2O$ as a good candidate for reduction of one of the most resilient compounds, namely $CO_2$. There is a need for a low cost, sustainable and highly efficient catalytic reduction of $CO_2$ into fuel (e.g., methanol or CO).

The present invention generally relates to methods of converting $CO_2$ into methanol or CO. The methods disclosed herein comprise (a) irradiating $CO_2$, water, $Cu_2O$, wherein the $Cu_2O$ comprises a (i i 0) facet to form methanol, and (b) irradiating $CO_2$, water, $Cu_2O$, wherein $MoS_2$ is adsorbed to the $Cu_2O$, wherein the $Cu_2O$ comprises a (i i 0) facet to form CO. These methods are useful as a sustainable source of energy and to mitigate $CO_2$ emissions. These methods can provide solar energy utilization, carbon capture technology, and low cost production of fuels (methanol and CO).

The use of the terms "a," "an," "the," and similar referents in the context of describing the invention (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the invention and is not a limitation on the scope of the invention unless otherwise claimed. No language in the specification should be construed as indicating any non-claimed element as essential to the practice of the invention. As used herein, the singular forms "a," "an," and "the" include plural referents unless the context clearly dictates otherwise. Thus, for example, the term "a material" is intended to mean one or more materials, or a combination thereof.

As used herein, the terms "about" and "approximately" generally mean plus or minus 10% of the stated value. For example, about 0.5 would include 0.45 and 0.55, about 10 would include 9 to 11, about 1000 would include 900 to 1100.

Preparation of $Cu_2O$

Figure 1:
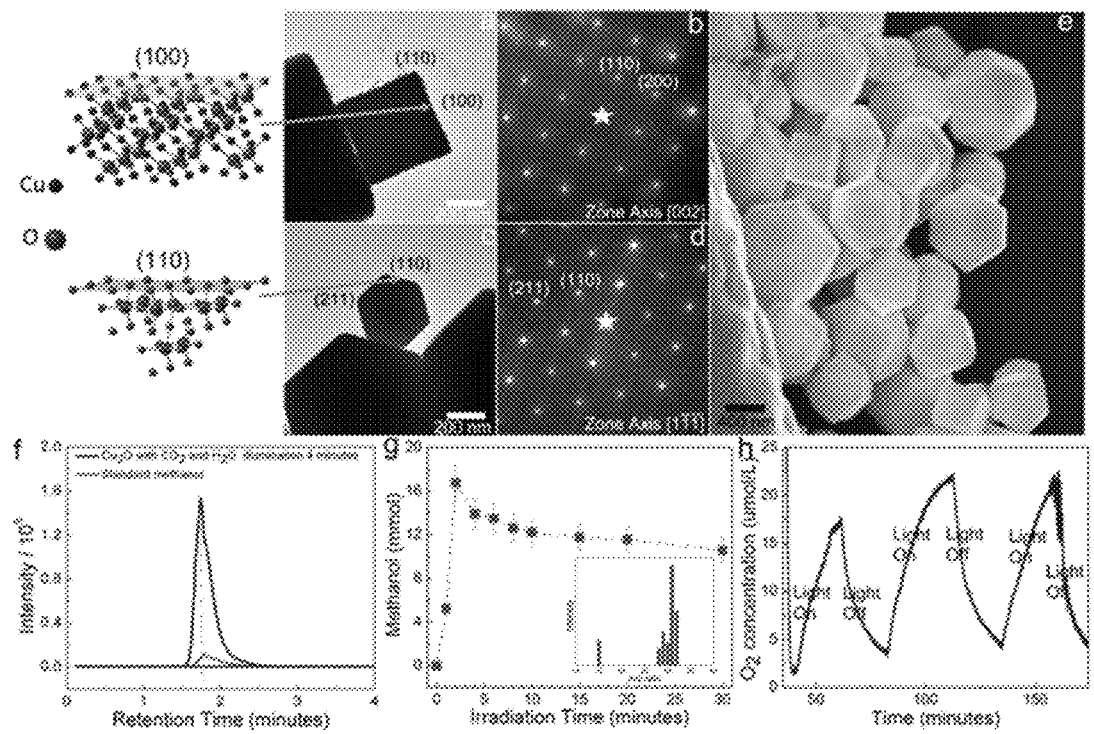
FIG. 1 shows the structure, characterization, and photocatalytic performance of the $Cu_2O$ particles. (Top left) Atomic model of Cu terminated by the (110) and (100) surface of $Cu_2O$ used for DFT calculations. (a) TEM image of a single cubic $Cu_2O$ nanocrystal with well-defined facets. (b) NBD from the edge of the nanocrystal in (a), indicated by the arrow. (c) TEM image of another particle with a hexagonal projected shape and well-defined facets. (d) NBD on the edge of (c), indicated by the arrow. (e) SEM image of the cubic/octahedral sample. (f) Methanol production by the cubic/octahedral sample measured by GC during the photocatalytic reaction as a function of retention time. (g) Illumination time dependent conversion of methanol produced by the photocatalytic reaction. Inset shows mass spectra of methanol obtained by GC/MS analysis of the photocatalytic reaction products. (h) $O_2$ evolution from the $CO_2$ reduction reaction during photocatalysis.

The $Cu_2O$ with (i i 0) facets provided herein can be prepared via colloidal synthesis by heating a mixture of copper acetate, sodium dodecyl sulfate, sodium hydroxide and D-(+)-glucose at 60° C. for 1 h. Two types of $Cu_2O$ samples can be synthesized by changing the precursors, one containing a mixture of cubic and octahedral nanocrystals and the other primarily composed of cubic nanocrystals. Characterization of the cubic/octahedral sample by TEM and SEM (FIG. 1c and FIG. 1e) showed various projections of $Cu_2O$ crystals with well-defined facets and noticeable truncations at the corners. Nanobeam electron diffraction (NBD) showed (110) and (200) facets with a [002] zone axis (FIG. 1b). This indicates that the particle shown in FIG. 1a is a cube enclosed by (100) facets with (110) facets at the truncated corners. Particles with a hexagonal projected shape were also observed (FIG. 1c), with a [1 $\bar{1}$ $\bar{1}$] zone axis, (110) edges, and (211) corners seen by NBD (FIG. 1d). All $Cu_2O$ crystals were cubic phase with space group Pn$\bar{3}$m, which were confirmed both by TEM and x-ray powder diffraction measurements. Scanning electron microscopy (SEM) showed the truncated cubic/octahedral crystals were 500 nm to 1 μm in size (FIG. 1e).

$CO_2$ Reduction to Methanol

The methods disclosed herein provide reduction of $CO_2$ to methanol. $Cu_2O$ having at least one (i i 0) facet (where i is 1-12) is irradiated, e.g., with visible to ultraviolet light, in the presence of $CO_2$ and $H_2O$ to form methanol. Benefits of the disclosed methods include, for example: (1) directly converting solar energy to liquid fuels without electricity input, which improves the conversion efficiency and lowers the cost; (2) the use of Earth-abundant elements (e.g., hydrogen, carbon, oxygen, and copper) which also lowers the cost for practical applications; (3) $Cu_2O$ has a band gap of 2.1 eV enabling the absorption of visible light, which constitutes most of the solar spectrum incident on Earth; (4) the method is stable and safe for large-scale production with $CO_2$ and $H_2O$ as inputs and methanol (or CO, in some specific cases) as outputs, with oxygen as a byproduct; (5) the disclosed methods involves the most efficient photocatalytic process known for conversion of $CO_2$ to methanol with a quantum yield of 72% and a solar to fuel efficiency equal to 27%.

As used herein, the term "$Cu_2O$" or "cuprous oxide" refers to forms of said compound, including but not limited to nano-objects, nanoparticles, nanostructures, nanocomposites, nanocrystals, nanotubes, nanosheets, nanowires, quantum dots, nanorods, bulk single crystals, or a mixture thereof. As used herein, a nanostructure or nanocomposite may comprise one or more materials and/or components. The $Cu_2O$ used in the disclosed methods has at least one (i i 0) facet, where i is 1-12. Thus, in some cases, the $Cu_2O$ has at least one facet selected from (1 1 0), (2 2 0), (3 3 0), (4 4 0), (5 5 0), (6 6 0), (7 7 0), (8 8 0), (9 9 0), (10 10 0), (11 11 0), and (12 12 0). In some cases, the $Cu_2O$ has at least one (1 1 0) facet. The shape of the $Cu_2O$ can be as octahedral, truncated cubic, or a mixture thereof. One $Cu_2O$ material is shown in FIG. 1b, in which the high index facet is a (110) facet shown in comparison to a $Cu_2O$ material containing a (100) facet shown in FIG. 1a.

Illumination of the same amount of cubic $Cu_2O$ sample in the presence of $CO_2$ and $H_2O$ produced only a fraction (~10%) of the methanol observed with the cubic/octahedral sample, suggesting that the (100) facets were nearly inactive whereas the sample with higher-index facets was more active photocatalytically.

Single $Cu_2O$ particles were assessed by both environmental transmission electron microscopy (ETEM) and scanning fluorescence x-ray microscopy (SFXM) in a novel nanoreactor while exposed to a mixture of gaseous $CO_2$, $H_2O$, and light. For example, a truncated hexagonal shaped particle (particle I) was identified by TEM. A corresponding single particle electron diffraction (SPED) measurement indicated the edges of particle I were {220} planes in the TEM view. Then, the nanoreactor containing the $Cu_2O$ particles was transferred from the ETEM to the SFXM platform.

Figure 2:
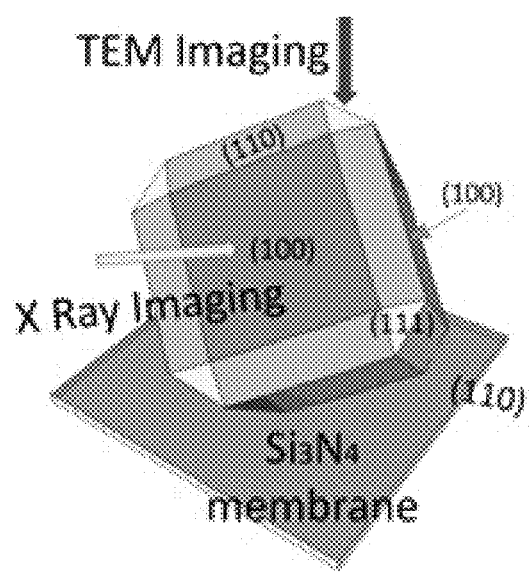
FIG. 2 is a schematic of the electron beam and x-ray directions for TEM and SFXM imaging on particle I, a truncated cube.
Figure 3:
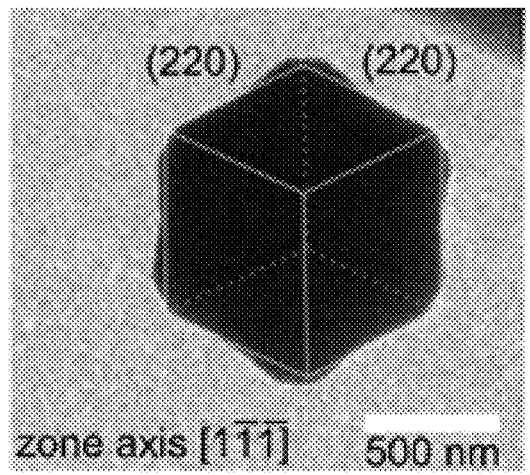
FIG. 3 is a TEM image of particle I with the electron beam parallel to the [1 1̄ 1̄] direction of the $Cu_2O$ cube.

Low-resolution scans using the Cu and Ni Kα fluorescence signals from the $Cu_2O$ particles and grid bars, respectively, allowed location of the same particle I for imaging and nano-spectroscopic study by SFXM. In the high resolution Cu Kα fluorescence, observe particle I as a truncated square rather than a truncated hexagon. This was due to the relative projected views of the particle using the ETEM and SFXM platforms, which differed by nearly 60°, and can be understood by considering particle I to be a cube resting on one of its truncated corners, a (111) facet, on the supporting $Si_3N_4$ membrane (FIG. 2). With the TEM view directions as indicated by the arrow, the particle appeared as a corner-truncated hexagon (FIG. 2, FIG. 3), while it presented as a corner-truncated square when viewed with x-rays (FIG. 2). Hence, the corner of particle I was a (110) facet while edges are exposed as a (100) facet along the x-ray view direction (FIG. 2). Particle I was checked again by TEM and SPED after the x-ray measurements, which showed that the location and structure of particle I were preserved. This rules out the possibility that the particle moved or was significantly damaged structurally by the x-ray beam. While characterization of the same $Cu_2O$ particles by both ETEM and SFXM was accomplished, it should be noted that in TEM, the particle could not be tilted to the same view orientation as for the SFXM measurements. Specific facets of particle I were targeted by directing the nano-focused x-ray beam parallel to them whilst scanning the incident x-ray energy, enabling the facet-dependent spectroscopic information of the Cu active sites to be obtained. The spectroscopic signal, which resulted from a columnar projection of the x-ray beam through the plane of the facet, contains information about local chemical state of the facet as well as the nearby bulk material beneath it. The observed spectra reflects an admixture of states resulting from both the surface and interior chemistry.

In various instances, a x-ray fluorescence spectra was taken near the Cu K-edge on the (110) facet of $Cu_2O$ particle I in its initial pristine state revealed a white-line peak at 8981.0 eV, indicating a $Cu^+$ oxidation state associated with this facet, in agreement with reference x-ray absorption spectra (XAS) taken from pure $Cu_2O$. By contrast, the white-line peak observed on the (100) facet was at 8981.5 eV, indicating the presence of both $Cu^+$ and $Cu^{2+}$ oxidation states. When measuring spectra on the (110) facet before and after flushing $CO_2/H_2O$ through the nanoreactor for a few min, the peak shifted between 1.0 and 1.5 eV toward higher energy, indicating the oxidation state of the Cu changed from $1^+$ toward $2^+$ due to the coadsorption of $CO_2/H_2O$. In addition, consecutive spectra measured at intervals of 10 min at another position on the (110) facet of particle I showed a gradual shift of the peak by ~1 eV until reaching saturation in about 1 h. These results suggest that $CO_2/H_2O$ coadsorbed on the (110) facet reduced the electron density of the exposed Cu atoms, causing the oxidation state to shift from $Cu^+$ to $Cu^{2+}$. Furthermore, when the particle was excited with a green laser (532 nm) while maintaining constant $CO_2/H_2O$ gas flow, the peak shifted ~1 eV toward lower energy, indicating that the majority of the Cu oxidation states shifted back to $Cu^+$. In comparison, the oxidation states of the Cu atoms on the (100) facet did not change upon $CO_2/H_2O$ adsorption in either the dark or the illuminated states, indicating the (100) facet was photocatalytic inactive. In successive measurements on several other similar $Cu_2O$ particles with similar spectroscopic shifts on (110) facets were reproducibly observed followed by reversion upon illumination, and statistically insignificant shifts on the (100) facets. The x-ray measurements could not have triggered the photocatalytic reaction because the chemical state of the Cu in the pristine $Cu_2O$ did not change over the course of many measurements without the introduction of gas, and it did not change from $Cu^{2+}$ to $Cu^+$ until subsequent optical illumination.

Figure 4:
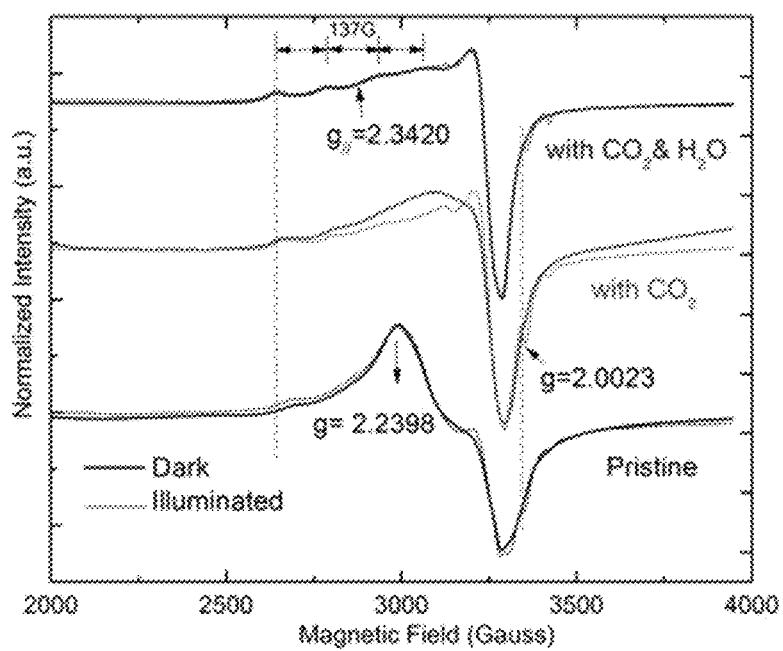
FIG. 4 is a dark EPR spectra (thicker solid lines) of $Cu_2O$ particles, showing electron transfer between $CO_2$ and $Cu_2O$ particle without illumination. Light-induced EPR spectra (thinner solid lines), showing electron transfer between $CO_2$ and the $Cu_2O$ particle with simulated sunlight illumination.

ETEM was used to examine another $Cu_2O$ particle in the nanoreactor, the truncated cube particle II, with the same orientation as particle I that was studied with x-rays since the particle could not be tilted to the same view orientation as for the SFXM measurements due to geometric limitations of the TEM instrument. SPED measurements confirmed the presence of (110) facets on the truncated corners and (100) facets on the faces of particle II, as with particle I in the x-ray measurements. Electron energy loss spectra (EELS) recorded on the (110) facet before and after $CO_2/H_2O$ coadsorption in the dark state showed that the Cu $L_{2,3}$-edge (2p to 3d transition) shifted ~2 eV toward lower energy upon $CO_2/H_2O$ adsorption. The EELS spectrum from the pristine particle is consistent with the peak position and $L_3/L_2$ peak intensity ratio of $Cu_2O$. The broadening of the spectrum recorded with gas flow and the decrease in the $L_3/L_2$ peak intensity ratio indicate the formation of $Cu^0$. The energy shift between the spectral peaks of the particles taken before and after gas adsorption shows that, of the superposition of copper phases present including metallic $Cu^0$. $Cu^{2+}$ dominates because the $L_3$ peak energies of $Cu^+$ and $Cu^+$ are the same. This was further quantified by electron paramagnetic resonance (ERR) with much higher sensitivity (FIG. 4). Density functional theory (DFT) calculations were carried out to understand the mechanism of $CO_2$ and $H_2O$ adsorption on $Cu_2O$ on different facets. The calculations showed that the coadsorption of $CO_2$ and $H_2O$ are thermodynamically favorable on both the (110) and (100) facets (Cu termination was considered for both facets), although the coadsorption on (110) is much more favorable ($E_{ad}$~-2.8 eV) than that on (100) ($E_{ad}$~-1.87 eV). It is notable that the coadsorption of $CO_2$ and $H_2O$ on Cu terminated (110) led to a dramatic change of the arrangement of Cu atoms on the surface leading to the formation of Cu clusters. This was confirmed by EPR measurements (FIG. 4) as described below. This cluster formation, however, did not occur on either the Cu/O terminated (the termination have both Cu and O atoms) (110) or the Cu terminated (100) upon $CO_2$ and $H_2O$ adsorption, based on our calculation. The DFT calculations show that the (110) facets of the synthesized $Cu_2O$ particles are Cu terminated, and therefore have greater photocatalytic activity for coadsorption of $CO_2$ and $H_2O$. The surface termination of $Cu_2O$ has a strong effect on the photocatalytic reaction activity and may affect the final product from the reaction.

While not being bound by theory, upon coadsorption of $CO_2/H_2O$ on $Cu_2O$ particles, intermolecular electron transfer can occur between the Cu active sites at the (110) surfaces and $CO_2$ molecules. This redistribution of electron density results in partial reduction of adsorbed $CO_2/H_2O$ molecules lowering the energy barrier for their complete reduction. On the other hand, the electron redistribution reduces the electron density of (110) surface. This in turn facilitates localization of photogenerated electrons on these sites, enhancing the probability of their interaction with adsorbed molecules. Illumination of $CO_2/H_2O$ coadsorbed on the (110) facet, therefore, leads to efficient electron transfer and removal of the bonding between $CO_2$ molecules and active sites, restoring the electron density of the pristine $Cu_2O$.

In order to investigate binding and electron transfer between Cu active sites and $CO_2$ molecules, EPR measurements were done on pristine $Cu_2O$ particles, exposed to $CO_2/H_2O$ in dark and illuminated conditions. The pristine particles (FIG. 4) showed the existence of $Cu^{2+}$ defects with unpaired electrons in 3d orbitals consistent with the p-doping of $Cu_2O$ nanoparticles. The spectral shape suggests the loosely packed pristine $Cu_2O$ powder aligned in the magnetic field (FIG. 4, pristine). In most cases, the isotropic spectrum of Cu complexes is characterized by the presence of $g_{//}$ at low field with the large contribution of $A_{//}$ hyperfine constant as a consequence of high spin density in $d_{(x^2-y^2)}$ orbital. However, in loosely packed powders (FIG. 4, pristine), field induced ordering of initial perfectly orientated powders can occur, causing deviation from the above described isotropic spectra. In this partially ordered system, the principle hyperfine peaks lose their intensity relatively to signals corresponding to the direction of maximum static susceptibility. Therefore, the hyperfine pattern of typical Cu complexes disappears in favor of a new single crystal signal at intermediate g with large and almost unresolved hyperfine splitting. Indeed, this kind of signal (FIG. 4, pristine) is observed in the $Cu_2O$ powders prior to treatment with $CO_2$. Upon $CO_2$ adsorption in dark, however, the anisotropy of the $Cu_2O$ powder spectrum, gradually disappears and a hyperfine pattern reappears (FIG. 4, with $CO_2$). The full isotropic spectrum of $Cu^{2+}$ is, however, restored only by $CO_2/H_2O$ coadsorption (FIG. 4, with $CO_2$ and $H_2O$). In this case, the restored g and A tensors provide evidence for distorted tetrahedral complex rather than octahedral or square planar coordination typically found for Cu complexes (experimental hyperfine $A_{//}$ for Cu of 137 G and g// tensor of 2.3420 were observed). The overall intensity of spectrum was increased suggesting the number of spins and consequently the number of $Cu^{2+}$ ions increased upon $CO_2$ and $H_2O$ co-adsorption in dark. This suggested $CO_2$ molecules are withdrawing electron density from $Cu^+$ active sites. This is consistent with our x-ray spectroscopic observation and structural information that the Cu oxidation states shifted from $Cu^+$ to $Cu^{2+}$ upon $CO_2/H_2O$ co-adsorption that electron density was pulled away from the $Cu_2O$ surface. A new small intensity peak with g factor at 2.0023 was observed with illumination of $Cu_2O$ at 4K (FIG. 4). This signal is originated from the conduction electrons in the metallic Cu clusters formed upon illumination. This indicated the formation of metallic Cu clusters and photogenerated holes observed as $Cu^{2+}$ on $Cu_2O$ particle surfaces under illumination. These Cu clusters may play important role in electron hole pair separation and catalytic conversion of $CO_2$ and $H_2O$ to methanol. The Cu clusters may come from the $Cu_2O$ disproportionation reaction, which has been quantified by EPR. The disproportionation reaction is seven orders less than the main photocatalytic reaction. Thus, the amount of Cu clusters present is seven orders of magnitude less than the amount of $O_2$. Hence, the observed $O_2$ evolution (FIG. 1h) does not only originate from $Cu^+$ disproportionation. This photo-induced disproportionation reaction can be mitigated by surface coating. In contrast to dark adsorption EPR measurements, the number of $Cu^{2+}$ ions decreased after illumination, suggesting conversion of $Cu^{2+}$ into non-paramagnetic $Cu^+$. This result is consistent with our previous observation that the Cu oxidation state shifted from $Cu^{2+}$ back to $Cu^+$ under illumination. This is also consistent with structural information that the electron densities contracted back to their original states under illumination. The EPR measurements have much higher sensitivity than the EELS and x-ray nanospectroscopy measurements performed here. The dominant ERR signal comes from $Cu^{2+}$ with only a small peak from the Cu dusters (about $4.98 \times 10^{-12}$ mol). The x-ray nanospectroscopy and EELS measurements only probed the dominant formation of $Cu^{2+}$ and were not sensitive enough to probe the formation of this small quantity of Cu clusters.

In some embodiments, the method of $CO_2$ reduction to methanol comprising the $Cu_2O$ suspended in water. In various cases, the $Cu_2O$ material is used in approximately a 1 mM to a 20 mM concentration. In some cases, the $Cu_2O$ material is used in approximately a 3 mM to a 15 mM concentration.

In some cases, the method comprises a $CO_2/H_2O$ mixture that is flowed into the $Cu_2O$ and water (optionally as a $Cu_2O$/water suspension) while irradiated. In some cases, the "$CO_2/H_2O$ mixture" is produced by flowing $CO_2$ through a $H_2O$ bubbler creating a mixture of water vapor and $CO_2$ gas.

In some cases, the method disclosed herein is performed at atmospheric pressure (e.g., about 1 bar). In some cases, the method is performed at elevated pressures (e.g., at a pressure greater than about 1.5 bar).

In various cases, the $CO_2$, $Cu_2O$, and water is irradiated by exposure to ultraviolet to visible Hall, for example via use of a xenon lamp. In some cases, the light used for irradiating can be selected to have one or more wavelengths from 200 to 650 nm. The light source for the irradiation can be, for example, a low pressure mercury lamp, a medium pressure mercury lamp, a high pressure mercury lamp, an ultrahigh pressure mercury lamp, an incandescent lamp, a xenon lamp, a halogen lamp, a carbon arc lamp, a metal halide lamp, a fluorescent lamp, a tungsten lamp, a gallium lamp, an excimer lamp, a pseudo sunlight source, the sun or any combination thereof. In some instances, the light can be from a 300 W xenon lamp used at a power of 204 W.

Illumination of (i i 0) faceted $Cu_2O$ nanoparticles in the presence of $CO_2$ and water vapor showed formation of methanol (see FIG. 1f), which was not produced if $Cu_2O$ was not present.

The amount of methanol produced can be determined by comparing the area under the curve of methanol GC peaks against that of known amounts of standard pure methanol. The methanol production and its dependence on irradiation time (FIG. 1g) showed up to a quantum efficiency of 72%. In some cases, the QE is at least 50%, at least 60%, or at least 70%.

The QE can be calculated based on the following formula $$QE = \frac{6 \times \text{the number of produced methanol molecules}}{qt_{irradiation}}$$

wherein the term "q" in equation 1 refers to a photon flux. The term "photon flux" refers to the number of photons per second per unit area equal to $1.099 \times 10^{-3}$ Einstein·s$^{-1}$ and the term "t" in equation 1 refers to a time of irradiation equal to 120 s. The number of methanol molecules is equal to 16 mmol of methanol produced.

The solar-to-fuel efficiency was measured to be 27%, which was close to the theoretical prediction of 34.5%. In some cases, the method of $CO_2$ reduction to methanol comprises a solar to fuel (STF) efficiency of at least 20%, wherein an AM 1.5G solar simulator is used as the light source. In some embodiments, the method of $CO_2$ reduction to methanol comprises a solar to fuel efficiency of at least 27%, wherein an AM 1.5G solar simulator is used as the light source. The STF can be calculated based on the following formula $$STF = \frac{\left[(CH_3OH \text{ mmol/s}) \times \Delta G\left(\frac{kJ}{mol}\right)\right]}{\left[P_{total}\left(\frac{mW}{cm^2}\right) \times \text{Area (cm}^2)\right]}$$

wherein the $\Delta G$ is 638.73 kJ/mol. The term "$P_{total}$" refers to an incident illumination power density equal to 25 mW/cm$^2$. The area refers to an irradiation area equal to 12.4 cm$^2$. The rate of methanol production can be obtained from experimental measurement. In some experiments, it was measured at 0.133 mmol/s—which provides a STF of 27%

Concomitantly, the system produced oxygen in synchrony with periodic illumination (FIG. 1h), indicating this new material can couple $H_2O$ oxidation with $CO_2$ reduction, functioning as an artificial leaf, albeit in sub-stoichiometric ratio. Sub-stoichiometric oxygen production was previously observed; its formation rate is typically several orders of magnitude smaller than those of the main catalytic products. Part of the photogenerated holes may be consumed in photo-induced disproportionation of $Cu_2O$ nanoparticles and/or in oxidation of methanol to other products, contributing to the steady state in the methanol evolution. If $O_2$ came from air leaking into the sealed reactor, the $O_2$ concentration should monotonically increase rather than be synchronized with the illumination. Thus, the $O_2$ (FIG. 1h) must come from the photocatalytic reaction other than air leaking.

CO$_2$ Reduction to CO

Further provided herein are methods of converting CO$_2$ to CO comprising irradiating CO$_2$, water, and MoS$_2$ adsorbed onto Cu$_2$O to form CO, wherein the Cu$_2$O has a (i i 0) facet and i is 1 to 12. The Cu$_2$O particles, their methods of preparation and physical analyses are discussed in detail in the above sections. For conversion of CO$_2$ to CO, the Cu$_2$O particles are further modified such that MoS$_2$ is adsorbed onto their surface. MoS$_2$ can be adsorbed onto a Cu$_2$O particle by chemical vapor deposition.

The MoS$_2$ adsorbed onto Cu$_2$O can be suspended in water. In some cases, the MoS$_2$ adsorbed onto Cu$_2$O is present at a concentration of 1 mM to a 20 mM, or 3 mM to a 15 mM.

The irradiation of the CO$_2$, water, and MoS$_2$ adsorbed onto CuO$_2$ can occur as discussed above for production of methanol.

MoS$_2$ coating changes the adsorption properties of H$_2$O on Cu$_2$O.

The invention will be more fully understood by reference to the following examples which detail exemplary embodiments of the invention. They should not, however, be construed as limiting the scope of the invention. All citations throughout the disclosure are hereby expressly incorporated by reference.

EXAMPLES

Materials:

Deionized water, Cu(CH$_3$COO)$_2$, sodium dodecyl sulfate, NaOH solution, and the D-(+)-glucose solution were obtained from Sigma-Aldrich (St. Louis, Mo., USA). The CO$_2$ gas was obtained from Airgas, Inc. The 300 W Xe lamp was obtained from Perkin-Elmer Optoelectronics, Waltham, Mass. Standard methanol (LC-MS ultra CHROMASOLV, tested for UHPLC-MS) was purchased from Fluka. Scanning electron microscopy (SEM) images of the photocatalyst particles were taken with a JEOL 7500 scanning electron microscope with an acceleration voltage of 10 kV. Nano-beam diffraction (NBD), EELS measurements, transmission electron microscope and high resolution TEM (HRTEM) images were performed with a JEOL 2100F operated at accelerating voltage of 200 kV and equipped with a Gatan imaging filter system at the CNM. Ex situ TEM characterization was performed by drop casting a suspension of the photocatalyst particles in ethanol onto a Formvar-coated Au TEM grid. The amount of methanol produced was measured using an Agilent Headspace sampler (Model 7697A) connected to an Agilent gas chromatograph/mass spectrum (GC/MS) analyzer (Model 5975C GCMS, triple-axis detector, DB-5MS column, and helium carrier gas).

Synthesis of Cu$_2$O Particles:

In a typical experiment to synthesize the truncated cubic and octahedral Cu$_2$O sample, deionized water (88.2 mL), Cu(CH$_3$COO)$_2$ aqueous solution (5 mL, 0.1 M), and sodium dodecyl sulfate (SDS, 0.87 g) were successively added into a three-neck flask. The three-neck flask was placed in a water bath at 60° C. with vigorous magnetic stirring. After complete dissolution of the SDS powder in 1 h, NaOH solution (1.8 mL, 1.0 M), and D-(+)-glucose aqueous solution (5 mL, 0.1 M) were successively quickly injected into the flask. The total volume of solution was 100 mL. The flask was kept in a water bath at 60° C. after the injection under vigorous magnetic stirring for 1 h. The solution color gradually changed from blue to green, yellow, orange, and finally turned to brick-red. After the reaction, the precipitate was separated from the solution by centrifugation at 5000 rpm for 5 min, and washed several times with deionized water/ethanol solution. All the particles have been washed and purified to remove ligands after the synthesis. Both samples were dried inside a N$_2$ gas flow glove box under room temperature for 48 h then stored inside the N$_2$ gas flow glove box to avoid any contamination from organic solvents.

Photocatalytic CO$_2$ Reduction:

In a typical experiment, the photocatalytic activity of the Cu$_2$O particle is characterized by measuring the methanol production. In a typical reaction, 0.01 g of purified particles were dispersed in 5 mL ultrapure deionized H$_2$O in a 20-mL Agilent Headspace vial and sealed. The suspension was thoroughly degassed to remove air with CO$_2$ gas for 10 min. CO$_2$ gas was bubbled through a deionized H$_2$O bubbler glassware for the formation of the CO$_2$/H$_2$O gas mixture. The suspension was continuously flushed with the CO$_2$/H$_2$O gas mixture for another 30 min to saturate the suspension with CO$_2$. Then the suspension was illuminated using a 300 W Xe lamp a power of 204 W with continuous CO$_2$/H$_2$O gas flow for 0-30 min. The sealed suspension was removed from the gas line after illumination.

Quantum Efficiency Determination:

Actinometry was used to determine the photon flux from the Xe lamp with the same power (204 W) and distance from the optical source to the sample for the photocatalytic reaction. Since Cu$_2$O has a band gap of 2.1 eV (~590 nm), iron (III) oxalate was chosen as the standard chemical actinometry followed by IUPAC'. Iron (III) oxalate hexahydrate (Fe$_2$(C$_2$O$_4$)$_3$.6H$_2$O), ammonium iron (II) sulfate hexahydrate ((NH$_4$)$_2$[Fe(SO$_4$)$_2$].6H$_2$O), 1, 10-phenathroline, sodium acetate (CH$_3$COONa), and sulfuric acid were purchased from Sigma Aldrich.

1, 10-phenathroline was used for photometric determination of Fe$^{2+}$ by forming [Fe(phen)$_3$]$^{2+}$, which has strong absorption at 510 nm. The molar absorptivity of [Fe(phen)$_3$]$^{2+}$ was determined by using ammonium iron (II) sulfate and 1, 10-phenathroline. 0.4 mM Fe$^{2+}$ iron solution was made freshly by dissolving 0.00392 g (NH$_4$)$_2$[Fe(SO$_4$)$_2$].6H$_2$O with 25 mL 0.05 M H$_2$SO$_4$ solution. Then 0, 0.75, 1.25, 1.75, 3 mL 0.4 mM Fe$^{2+}$ solution were added to a series 25 mL volumetric flasks and mixed with 1.25 mL 0.5 M H$_2$SO$_4$, 6.25 mL buffer solution (stock solution: 3.82 g NaC$_2$H$_5$CO$_2$, 0.4 mL concentrated H$_2$SO$_4$, dilute to 40 mL with deionized water), 5 mL of 0.1% 1, 10-phenantroline solution (stored in the dark) and dilute to 25 mL with deionized water. The mixture was kept in the dark for about 60 min when full color development was achieved. The mixture contained concentrations of [Fe(phen)$_3$]$^{2+}$ ions ranging from 0 to 4.8×10$^{-5}$ M. The molar absorptivity c of [Fe(phen)$_3$]$^{2+}$ was determined to be 0.89×10$^4$ L·cm$^{-1}$·mol$^{-1}$ by measuring the concentration dependent absorbance at 510 nm, which is close to the suggested value (1.1×10$^4$ L·cm$^{-1}$·mol$^{-1}$).[1] This measured value was used for calculating the photon flux from the white light source.

A 0.006 M Fe$^{3+}$ solution was prepared by dissolving 0.05806 g Fe(C$_2$O$_4$)$_3$.6H$_2$O in 2 mL H$_2$SO$_4$ (0.5 M) and dilution with deionized water to 20 mL. Then 3 mL (V$_1$) of the solution was illuminated for certain amount of time (5, 15, 25, 30, 35 s) under efficient magnetic stirring with the white light source power at 204 W (the same power for the photocatalytic activity measurement). A 1 mL volume (V$_2$) of the illuminated solution was added to a 10 mL (V$_3$) volumetric flask containing a mixture of 5 mL of 0.1% 1, 10-phenantroline solution (stored in the dark), and 0.5 mL buffer solution, which was then diluted to a total volume of 10 mL. A reference sample was prepared in the same way except it wasn't illuminated. The production of $Fe^{2+}$ from $Fe^{3+}$ can be summarized by the following photochemical reaction.

$$2[Fe(C_2O_4)_3]^{3-} + h\nu \rightarrow 2[Fe(C_2O_4)_2]^{2-} + 2CO_2 + C_2O_4^{2-} \quad 5$$

All the solutions were stored in the dark for about 60 min until full color development was achieved. The absorbance difference between experimental samples and the reference sample was measured at 510 nm [optical path length l=1 cm, $\varepsilon(510 \text{ nm}) = 0.89 \times 10^4 \text{ L} \cdot \text{cm}^{-1} \cdot \text{mol}^{-1}$]. A 0.2 mL volume ($V_4$) of solution was taken from 10 mL ($V_3$) of fully developed solution then diluted to 3.2 mL ($V_5$) in an optical cuvette to ensure absorbance A (510 nm) within the range of 0.3-1.1. The number of moles of $Fe^{2+}$ produced by the photochemical reaction is given by $$n = \frac{\Delta A V_1 V_3 V_5}{\varepsilon l V_2 V_4}$$

The photon flux q (Einstein·s$^{-1}$) entering the sample cell is $$q = \frac{n}{t\Phi} = \frac{\Delta A V_1 V_3 V_5}{t\Phi \varepsilon l V_2 V_4}$$

and the slope of $$\frac{n}{t}$$

was measured as $9.28661 \times 10^{-4}$ mol·s$^{-1}$, since $\Phi_{Fe2+}$ (510 nm)=84.5%$^2$, q is calculated to be $1.099 \times 10^{-3}$ Einstein·s$^{-1}$ for the white light source at 204 W.

The quantum efficiency (QE) of methanol production is given by $$QE = \frac{6 \times \text{the number of produced methanol molecules}}{qt_{irradiation}}$$

when $t_{irradiation}=120$ s, 16 mmol methanol produced (FIG. 1g), the maximum QE at 510 nm wavelength is given by $$QE = \frac{6 \times 16 \times 10^{-3}}{1.099 \times 10^{-3} \times 120} = 72.8\%$$

Solar-to-Fuel Efficiency Determination:

The solar energy conversion was evaluated using AM 1.5G solar simulator as the light source with $Cu_2O$ photocatalyst (0.01 g photocatalyst in 20 mL DI water). The incident illumination power density $P_{total}$ was 25 mW/cm$^2$ and the irradiation area was 12.4 cm$^2$. The rate of methanol production from photocatalytic measurement was 0.133 mmol/s. Methanol and oxygen were measured as reaction products. A possible chemical formula describing the reaction is the following:

$$CO_2 + 2H_2O \rightarrow CH_3OH + \frac{3}{2}O_2$$

The Gibbs energy of this formula was suggested to be 638.73 kJ·mol$^{-1}$ $^3$. The solar to fuel efficiency was adopted from reference 4.

$$STF = \left[ \frac{(CH_3OH \text{ mmol/s}) \times \Delta G\left(\frac{kJ}{mol}\right)}{P_{total}\left(\frac{mW}{cm^2}\right) \times \text{Area (cm}^2)} \right] AM\ 1.5G$$

Thus, the solar to fuel efficiency was calculated as follows $$STF = \frac{0.133 \times 638.73}{25 \times 12.4} = 27.4\%$$

The Method of $CO_2$ Reduction to CO:

A two-furnace double-quartz-tube system was applied to control the temperatures of $MoO_3$ and S separately. Growth was carried out on silicon wafer (SiO/Si—Si with 285 nm of $SiO_2$). After they were cleaned with acetone, $Cu_2O$ powder was dispersed into ethanol solution and then drop coated onto the substrate and allowed to dry. Then it gives a fairly good binding between the $Cu_2O$ powder and the substrate. Substrates were then placed vertically into the center of the outer quartz tube. A 500-1000 mg portion of molybdenum (VI) oxide (MoO) powder (99.5% Sigma-Aldrich) powder was scattered 2-3.5 cm off the starting point of the high-temperature zone; 600 mg of sulfur powder (99.5%, Sigma-Aldrich) was put upstream in the outer one in quartz tube, right in the center of the low temperature zone. Argon was used to protect the system from oxygen and carry sulfur vapor from the upstream of the low temperature tube for reaction. The CVD system was first flushed with 500 sccm of Ar gas for 30 min, with both furnaces kept at room temperature. Then the flow rate was adjusted to 150 sccm of Ar gas, while the low-temperature furnace was heated up at first at 15° C./min to 180° C. and then at 1° C./min to 200° C.; the high-temperature furnace was heated to 866° C. at 40° C./min, dwell after reaching set temperature, and the total duration was 50 min. Afterward the flow rate was set at 50 sccm of Ar gas at a growth temperature at 866° C. for 20 min. After growth the residual sulfur powder was flushed with 500 sccm of Ar gas for 15 min by setting the low temperature furnace at 420° C. (40° C./min) while the temperature of the high-temperature furnace remained at 700° C., followed by fast cooling of the system with 500 sccm of Ar gas.

REFERENCES

1. Kuhn, H., et al., *Pure Appl. Chem.* 76, 2105-2146 (2004).
2. Demas, J., et al., *J. Phys. Chem.* 85, 2766-2771 (1981).
3. Singh, M., et al., *Proc. Natl. Acad. Sci.* 112, E6111-E6118 (2015).
4. Chen, Z. et al., *J. Mater. Res.* 25, 3-16 (2010).

What is claimed:

1. A method of converting $CO_2$ to methanol comprising irradiating $CO_2$, water, and a catalyst consisting essentially of $Cu_2O$ nanoparticles having a (i i 0) facet to photocatalytically form methanol, wherein i is 1 to 12.

2. The method of claim 1, wherein the irradiating comprises exposure to ultraviolet to visible light.

3. The method of claim 1, wherein the irradiating comprises exposure to light having one or more wavelengths from 200 to 650 nm.

4. The method of claim 1, wherein the water is present as a liquid.

5. The method of claim 1, wherein the water is present as water vapor.

6. The method of claim 1, wherein the (i i 0) facet is a (110) facet.

7. The method of claim 6, wherein the $Cu_2O$ nanoparticles having a (110) facet are octahedral, truncated cubic, or a mixture thereof.

8. The method of claim 7, wherein the irradiating comprises exposure to ultraviolet to visible light.

9. The method of claim 8, wherein the irradiating comprises exposure to light having one or more wavelengths from 200 to 650 nm.

10. The method of claim 1, where the method exhibits a quantum efficiency of at least 50%.

11. The method of claim 10, wherein the quantum efficiency is at least 70%.

12. The method of claim 1, wherein the $CO_2$ is continuously flowed through a suspension of the $Cu_2O$ nanoparticles in water during the irradiating.

13. The method of claim 1, wherein the $Cu_2O$ nanoparticles having a (i i 0) facet are prepared by a method comprising admixing copper acetate, sodium hydroxide, glucose, and a surfactant and heating the admixture to 60° C. for 30-90 minutes to form the $Cu_2O$ nanoparticles having a (i i 0) facet.

14. The method of claim 13, wherein the surfactant comprises sodium dodecyl sulfate.

15. A method of converting $CO_2$ to CO comprising irradiating $CO_2$, water, and a catalyst consisting essentially of $MoS_2$ adsorbed onto $Cu_2O$ nanoparticles to photocatalytically form CO,
wherein the $Cu_2O$ nanoparticles have a (i i 0) facet, and i is 1 to 12.

16. The method of claim 15, wherein the irradiating comprises exposure to ultravisible to visible light.

17. The method of claim 15, wherein the irradiating comprises exposure to light having one or more wavelengths from 200 to 650 nm.

18. The method of claim 15, wherein the (i i 0) facet is a (110) facet.

19. The method of claim 15, wherein the $Cu_2O$ nanoparticles having a (i i 0) facet are octahedral, truncated cubic, or a mixture thereof.

20. The method of claim 15, wherein the $Cu_2O$ nanoparticles having a (i i 0) facet are prepared by a method comprising admixing copper acetate, sodium hydroxide, glucose, and a surfactant and heating the admixture to 60° C. for 30-90 minutes to form the $Cu_2O$ nanoparticles having a (i i 0) facet.

* * * * *